(12) United States Patent
Bertolini et al.

(10) Patent No.: US 6,350,873 B2
(45) Date of Patent: Feb. 26, 2002

(54) PROCESS FOR PREPARING 5'-ACETYLSTAVUDINE

(75) Inventors: Giorgio Bertolini; Marco Frigerio, both of Milan; Maurizio Velati, Pavia; Luigi Petrucciani, Varese, all of (IT)

(73) Assignee: Clariant Life Science Molecules (Italy) S.p.A., Milan (IT)

( * ) Notice: Subject to any disclaimer, the term of this patent is extended or adjusted under 35 U.S.C. 154(b) by 0 days.

(21) Appl. No.: 09/834,028

(22) Filed: Apr. 12, 2001

(51) Int. Cl.[7] .............................................. C07D 239/54
(52) U.S. Cl. ...................................................... 544/310
(58) Field of Search .......................................... 544/310

(56) References Cited

PUBLICATIONS

Amino, Y et al, Chem. Pharm. Bull., 39, 1991, 622–625.*
Talekar, R.R. et al, Synthesis, 1993, 303–306.*

* cited by examiner

Primary Examiner—Mukund J. Shah
Assistant Examiner—Thomas McKenzie
(74) Attorney, Agent, or Firm—Scott E. Hanf

(57) ABSTRACT

The present invention relates to a process for preparing 5'-acetylstavudine, an intermediate which is useful in the preparation of 2',3'-didehydro-3'-deoxythymidine, an active principle with antiviral action which is commonly known as stavudine (D4T).

13 Claims, No Drawings

PROCESS FOR PREPARING 5'-ACETYLSTAVUDINE

The present invention relates to a process for preparing 5'-acetylstavudine, an intermediate which is useful in the preparation of 2',3'-didehydro-3'-deoxythymidine, an active principle with antiviral action which is commonly known as stavudine (D4T).

TECHNICAL FIELD OF THE INVENTION

Many processes for preparing stavudine have been described in the literature, such as, for example, those reported in: EP-A-0 340 778, EP-A-0 493 602, EP-A-0 501 511, WO 92/09599, EP-A-0 334 368, EP-A-0 519 464, EP-A-0 653 435, EP-A-0 653 436, EP-A-0 735 044, in Mansuri et al., J. Org. Chem. 1989, 54, 4780–4785 and in Classon et al., Acta Chem. Scand., B36, 1982, 251. Among these, EP-A-0 334 368, Mansuri et al. and Classon et al. describe the preparation of stavudine by deacetylation of 5'-acetylstavudine; in greater detail, both EP-A-0 334 368 and Mansuri et al. describe a process for preparing 5'-acetylstavudine (B) by reductive elimination of 2'-deoxy-2'-bromo-3',5'-diacetyl-5-methyluridine (A) in the presence of zinc as reducing agent and copper as activating agent, according to the reaction scheme given below.

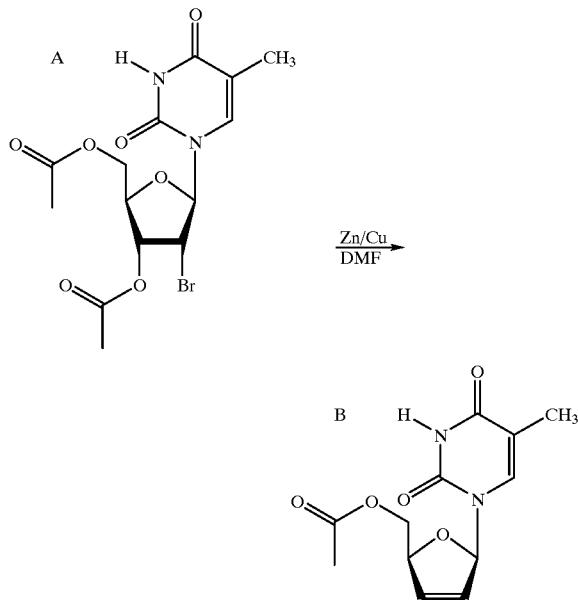

5'-Acetylstavudine is then converted into the final product by hydrolysis with sodium methoxide in methanol. The synthetic scheme described in Classon et al. is substantially identical, the only difference being that the reductive elimination reaction is carried out in the presence of zinc as reducing agent and acetic acid as activating agent.

However, the two synthetic processes described above are relatively unsatisfactory, in particular on account of the reductive elimination reaction which gives only moderate yields and, thus, is difficult to apply at the industrial level; the purpose of the present invention is thus to find a process which allows the reductive elimination of 2'-deoxy-2'-bromo-3',5'-diacetyl-5-methyluridine in yields greater than those of the processes known in the art.

DESCRIPTION OF THE INVENTION

A process has now been found, and this constitutes the subject of the present invention, which makes it possible to prepare 5'-acetylstavudine in yields that are substantially greater than those of the processes described above; according to this process, 2'-deoxy-2'-bromo-3',5'-diacetyl-5-methyluridine is converted into 5'-acetylstavudine by reductive elimination in the presence of zinc as reducing agent combined with an ammonium salt or a phosphonium salt as activating agent.

Among the various ammonium salts, the ones that are particularly preferred are the halides and sulphates; among the halides, those that are most indicated for carrying out the invention are selected from tributylamine hydrochloride, triethylamine hydrochloride, ammonium chloride, tributylamine hydrobromide, triethylamine hydrobromide and/or ammonium bromide.

Among the phosphonium salts, the ones that are preferred are the halides, in particular the bromides, for example such as triphenylphosphine hydrobromide.

As will be seen from the examples which follow, and which should be considered as purely illustrative of and non-limiting on the invention, zinc is generally used in an amount of between 1 and 4 equivalents and preferably between 1.5 and 2.4 equivalents, while the ammonium salt is used in an amount of between 0.2 and 2 equivalents and preferably between 0.5 and 1.5 equivalents.

The process according to the present invention may be carried out in the usual organic solvents used in reductive eliminations, such as alcohols, ethers, esters or dipolar aprotic solvents; among these, the preferred solvents are dipolar aprotic solvents such as, for example, DMF or DMSO and ethereal solvents such as, for example, THF, or mixtures thereof.

In the preferred embodiment of the invention, 1.5–2.4 equivalents of zinc powder are added to a solution at 20° C. of 2'-deoxy-2'-bromo-3',5'-diacetyl-5-methyluridine in DMF, DMSO or THF, or mixtures thereof. The reaction mixture is left stirring for about 10 minutes and 0.5–1.5 equivalents of the ammonium salt, preferably tributylamine hydrochloride, triethylamine hydrochloride, ammonium chloride, tributylamine hydrobromide, triethylamine hydrobromide or ammonium bromide, are then added; the system is then left to react at 30° C. for about 2 hours, until the reaction is complete.

As may be appreciated from the examples attached, the process according to the present invention allows the production of 5'-acetylstavudine in particularly high yields when compared those of processes known in the prior art; specifically, 5'-acetyl-10 stavudine may be obtained in yields of 56–67% working with 86–90 g of 2'-deoxy-2'-bromo-3', 5'-diacetyl-5-methyluridine and in yields of greater than 70% by working with about 10 g of starting material; in contrast, the processes described in EP-A-0 334 368, Mansuri et al. and Classon et al. give yields of 44–52% by working using substantially smaller starting amounts of 2'-deoxy-2'-bromo-3',5'-diacetyl-5-methyluridine, that is to say more or less of the order of 1.6–2 g.

The 5'-acetylstavudine obtained according to the process of the present invention may then be converted into stavudine according to the various processes known in the art, such as, for example, those disclosed in EP-A-0 334 368, Mansuri et al. and Classon et al., which should thus be considered as included in the present description also as regards the preparation of 2'-deoxy-2'-bromo-3',5'-diacetyl-5-methyluridine.

EXAMPLE 1

Zinc powder (352 g) is added to a solution of 2'-deoxy-2'-bromo-3',5'-diacetyl-5-methyl-uridine (90.8 g) in DMF (998 ml) at 20° C. The reaction mixture is left stirring for 10 minutes. Ammonium chloride (13.1 g) is then added. An exothermic reaction takes place, the temperature rises spontaneously to 35–40° C. and the system is left to react at 30° C. The solid is filtered off and the DMF is evaporated off under vacuum at 60–65° C. to give a dense oil. This material is taken up in tetrahydrofuran (700 ml) and stirred for 2 hours. The precipitate is filtered off and washed with tetrahydrofuran (100 ml). The solution thus obtained is evaporated to dryness and the solid thus obtained is taken in isopropanol (450 ml) and heated to reflux, distilling off the head fractions up to the boiling point of the isopropanol. The mixture is cooled slowly to 20–25° C. and left stirring at this temperature for 3 hours. The solid thus obtained is filtered off and washed with isopropanol (50 ml). The wet solid thus obtained is redissolved in hot isopropanol, decolorized with charcoal, filtered, left to cool slowly and allowed to crystallize at 20–25° C. The solid is filtered off, washed with isopropanol and dried under vacuum at 60° C. to give 34.2 g of acetylstavudine (yield relative to the theoretical amount=57.3%).

EXAMPLE 2

Zinc powder (20.8 g) is added to a solution of 2'-deoxy-2'-bromo-3',5'-diacetyl-5-methyluridine (86 g) in DMF (946 ml) at 20° C. The reaction mixture is left stirring for 10 minutes. Triethylamine hydrochloride (14.6 g) is then added. An exothermic reaction takes place, the temperature rises spontaneously to 35–40° C. and the system is left to react at 30° C. The solid is filtered off and the DMF is evaporated off under vacuum at 60–65° C. to give a dense oil. This material is taken up in tetrahydrofuran (700 ml) and stirred for 2 hours. The precipitate is filtered off and washed with tetrahydrofuran (100 ml). The solution thus obtained is evaporated to dryness and the solid thus obtained is redissolved in isopropanol (200 ml) and this solution is evaporated under vacuum. The residue is taken up in isopropanol (400 ml) and heated to reflux, distilling off the head fractions up to the boiling point of the isopropanol. The mixture is cooled slowly to 20–25C and left stirring at this temperature for 3 hours. The solid thus obtained is filtered off and washed with isopropanol (75 ml). The wet solid thus obtained is redissolved in hot isopropanol, decolorized with charcoal, filtered while hot, left to cool slowly and allowed to crystallize at 20–25° C. The solid is filtered off, washed with isopropanol and dried under vacuum at 60° C. to give 33.8 g of acetylstavudine (yield relative to the theoretical amount=60%).

EXAMPLE 3

2'-Deoxy-2'-bromo-3',5'-diacetyl-5-methyluridine (86 g) is dissolved in THF (1l) at 20±5° C. and zinc powder (28.8 g) is then added. The reaction mixture is left stirring for 15 minutes. Tributylamine hydrochloride (70.6 g) dissolved in THF (290 ml) is added as quickly as possible. An exothermic reaction takes place. The reaction mixture is stirred at 30° C. until the reaction is complete, and is then cooled to 20° C. and stirred for 2 hours at this temperature, after which the suspension is filtered through Celite and washed with THF (100 ml). The solution thus obtained is evaporated under vacuum at 40° C. The solid thus obtained is taken up in isopropanol (150 ml) and concentrated under vacuum at 40° C., and the operation is repeated with further isopropanol (150 ml).

The residue thus obtained is taken up in isopropanol (400 ml) and heated to reflux until completely dissolved. This solution is cooled slowly to 20° C. and left stirring at this temperature for 3 hours. The solid is filtered off and washed with isopropanol (70 ml). The wet solid thus obtained is redissolved in hot isopropanol, left to cool slowly to 20–25° C. and stirred at this temperature. The solid is filtered off, washed with isopropanol (70 ml) and dried under vacuum at 50° C. to give 31.8 g of acetylstavudine (yield relative to theoretical amount=56.3%).

EXAMPLE 4

Zinc powder (32.3 g) is added to a solution of 2'-deoxy-2'-bromo-3',5'-diacetyl-5-methyluridine (100 g) in THF (1.4 l) and DMSO (80 ml) at 20° C. The reaction mixture is left stirring for 10 minutes. Tributylamine hydrochloride (78.4 g) is then added. An exothermic reaction takes place, the temperature rises spontaneously to 35–40° C. and the system is left to react at 30° C. until the reaction is complete. The solid is filtered off and the THF is evaporated off under vacuum at 60–65° C. to give a dense oil. The residue thus obtained is taken up in isopropanol (2×150 ml) and this solution is evaporated under vacuum. The residue is taken up in isopropanol (465 ml) and the solution is brought to reflux. The mixture is cooled slowly to 20–25° C. and left stirring at this temperature for 3 hours. The solid thus obtained is filtered off and washed with isopropanol (100 ml). The wet solid thus obtained is redissolved in hot isopropanol, decolorized with charcoal, filtered while hot, left to cool slowly and allowed to crystallize at 20–25° C. The solid is filtered off, washed with isopropanol (100 ml) and dried under vacuum at 60° C. to give 41.0 g of acetylstavudine (yield relative to the theoretical amount=65.4%).

EXAMPLE 5

Zinc powder (32.3 g) is added to a solution of 2'-deoxy-2'-bromo-3',5'-diacetyl-5-methyluridine (100 g) in THF (1.4 l) and DMSO (80 ml) at 20° C. The reaction mixture is left stirring for 10 minutes. Tributylamine hydrobromide (98.5 g) is then added. An exothermic reaction takes place, the temperature rises spontaneously to 35–40° C. and the system is left to react at 30° C. until the reaction is complete. The solid is filtered off and the THF is evaporated off under vacuum at 60–65° C. to give a dense oil. The residue thus obtained is taken up in isopropanol (2×150 ml) and this solution is evaporated under vacuum. The residue is taken up in isopropanol (465 ml) and the solution is brought to reflux. The mixture is cooled slowly to 20–25° C. and left stirring at this temperature for 3 hours. The solid thus obtained is filtered off and washed with isopropanol (100 ml). The wet solid thus obtained is redissolved in hot propanol, decolorized with charcoal, filtered while hot, left to cool slowly and allowed to crystallize at 20–25° C. for 3 hours. The solid is filtered off, washed with isopropanol (100 ml) and dried under vacuum at 60° C. to give 42.1 g of acetylstavudine (yield relative to the theoretical amount=67%).

EXAMPLE 6

In order to ascertain the possible influence of the acid activator on the yield of the reductive elimination reaction of 2'-deoxy-2'-bromo-3',5'-diacetyl-5-methyluridine, the reaction in the presence of zinc/triethylamine hydrochloride was compared with a similar reaction carried out in the presence of zinc/trifluoroacetic acid; the trifluoroacetic acid was used at a concentration such as to minimize the pH measured in an aqueous solution of triethylamine hydrochloride (pH 5.6±0.2) at a concentration of 5.1 g/110 ml.

Reaction with triethylamine hydrochloride

Zinc powder (3.2 g) is added to a solution of 2'-deoxy-2'-bromo-3',5'-diacetyl-5–20 methyluridine (10 g ) in 110 ml of DMF at 20° C. The reaction mixture is left stirring for 10 minutes. Triethylamine hydrochloride (5.1 g) is then added. An exothermic reaction takes place and the temperature rises spontaneously to 35–40° C. This mixture is left to react at 30° C. for 3 hours. At the end of the 3 hours, the conversion of the 2'-deoxy-2'-bromo-3',5'-diacetyl-5-methyluridine into 5'-2 5 acetylstavudine was evaluated by HPLC. HPLC analysis (percentage areas): 2'-deoxy-2'-bromo-3',5'-diacetyl-5-methyluridine (starting material)<0.5%, acetylstavudine 78.7%. Conversion yield determined by HPLC titre=73%.

Reaction with trifluoroacetic acid

Zinc powder (3.2 g) is added to a solution of 2'-deoxy-2'-bromo-3',5'-diacetyl-5-methyluridine (10 g) in 110 ml of dimethylformamide at 20° C. The reaction mixture is left stirring for 10 minutes. Trifluoroacetic acid is then added (1 ml of a 0.003% solution of trifluoroacetic acid in dimethylformamide). The amount of trifluoroacetic acid is that required to reproduce the calculated pH generated by the triethylamine hydrochloride under the conditions described in the above experiment. The reaction mixture is stirred for 15 minutes, without any increase in temperature being observed. The reaction mixture is then heated to 30–35° C. for 3 hours. At the end of the 3 hours the conversion of the 2'-deoxy-2'-bromo-3',5'-diacetyl-5-methyluridine into 5'-acetylstavudine was evaluated by HPLC, and it was found that no conversion 2'-deoxy-2'-bromo-3',5'-diacetyl-5-methyluridine into 5'-acetylstavudine had taken place (HPLC analysis of the reaction mixture: no acetylstavudine detectable).

Conclusions

As may be readily observed by the comparison between the yield for the reaction carried out in the presence of zinc/triethylamine hydrochloride (73%) and that for the reaction carried out in the presence of zinc/trifluoroacetic acid (no product formed), it may reasonably be concluded that the acidity of the reaction medium does not play an important role in activating the reductive elimination reaction of 2'-deoxy-2'-bromo-3',5'-diacetyl-5-methyluridine.

EXAMPLE 7

Zinc powder (3.2 g) is added to a solution of 2'-deoxy-2'-bromo-3',5'-diacetyl-5-methyluridine (10 g) in THF (142 ml) and DMSO (8 ml) at 20° C. The reaction mixture is stirred for 10 minutes. Triphenylphosphine hydrobromide (12.1 g) is then added. An exothermic reaction takes place, the temperature rises spontaneously to 35–40° C. and the system is left to react at 30° C. until reaction is complete. At the end of the three hours, the conversion of the 2'-deoxy-2'-bromo-3',5'-diacetyl-5-methyluridine into 5'-acetylstavudine was evaluated by HPLC. Conversion yield determined by HPLC titre=65%.

What is claimed is:

1. Process for preparing 5'-acetylstavudine, in which 2'-deoxy-2'-bromo-3',5'-diacetyl-5-methyluridine is converted into 5'-acetylstavudine in the presence of zinc as reducing agent combined with an activating agent, characterized in that the said activating agent is an ammonium salt and/or a phosphonium salt.

2. Process according to claim 1, characterized in that the said ammonium salt is a halide and/or a sulphate.

3. Process according to claim 2, characterized in that the said ammonium halide is a chloride and/or a bromide.

4. Process according to claim 1, characterized in that the said ammonium salt is selected from tributylamine hydrochloride, triethylamine hydrochloride, ammonium chloride, tributylamine hydrobromide, triethylamine hydrobromide and/or ammonium bromide.

5. Process according to claim 1, characterized in that the said phosphonium salt is a halide, preferably a bromide.

6. Process according to claim 5, characterized in that the said phosphonium bromide is triphenylphosphine hydrobromide.

7. Process according to claim 1, characterized in that zinc is present in an amount of between 1 and 4 equivalents and in that the said ammonium salt is present in an amount of between 0.2 and 2 equivalents.

8. Process according to claim 7, characterized in that zinc is present in an amount of between 1.5 and 2.4 equivalents and in that the said ammonium salt is present in an amount of between 0.5 and 1.5 equivalents.

9. Process according to claim 1, characterized in that it is carried out in a dipolar aprotic solvent or an ethereal solvent, or in mixtures thereof.

10. Process according to claim 9, characterized in that the said dipolar aprotic solvent is selected from DMF and/or DMSO.

11. Process according to claim 9, characterized in that the said ethereal solvent is THF.

12. Process according to claim 9, characterized in that the said solvent is a THF/DMF or THF/DMSO mixture.

13. Process for preparing stavudine, comprising a process according to any one of the preceding claims.

* * * * *